US012595212B2

(12) United States Patent
Ho et al.

(10) Patent No.: US 12,595,212 B2
(45) Date of Patent: Apr. 7, 2026

(54) TWO-STAGE SINTERING METHOD FOR PREPARING POROUS BIPHASIC CALCIUM PHOSPHATE CERAMIC FROM CALCIUM-CONTAINING BIOLOGICAL WASTE

(71) Applicant: Council of Agriculture, Executive Yuan, Taipei (TW)

(72) Inventors: Wen-Fu Ho, Kaohsiung (TW); Hsueh-Chuan Hsu, Taichung (TW); Shih-Ching Wu, Taichung (TW)

(73) Assignee: Council of Agriculture, Executive Yuan, Taipei (TW)

( * ) Notice: Subject to any disclaimer, the term of this patent is extended or adjusted under 35 U.S.C. 154(b) by 386 days.

(21) Appl. No.: 17/815,218

(22) Filed: Jul. 27, 2022

(65) Prior Publication Data

US 2023/0062742 A1 Mar. 2, 2023

(30) Foreign Application Priority Data

Aug. 12, 2021 (TW) ................................. 110129795

(51) Int. Cl.
| | |
|---|---|
| *C04B 35/447* | (2006.01) |
| *A61K 6/838* | (2020.01) |
| *A61L 27/12* | (2006.01) |
| *C04B 35/64* | (2006.01) |
| *C04B 38/00* | (2006.01) |
| *C04B 38/06* | (2006.01) |

(52) U.S. Cl.
CPC ............ *C04B 35/447* (2013.01); *A61K 6/838* (2020.01); *A61L 27/12* (2013.01); *C04B 35/64* (2013.01); *C04B 38/0054* (2013.01); *C04B 38/0645* (2013.01); *C04B 2235/447* (2013.01); *C04B 2235/48* (2013.01); *C04B 2235/6567* (2013.01); *C04B 2235/661* (2013.01)

(58) Field of Classification Search
None
See application file for complete search history.

(56) References Cited

U.S. PATENT DOCUMENTS

| | | | | |
|---|---|---|---|---|
| 5,922,025 A | * | 7/1999 | Hubbard | ............... A61L 27/446 |
| | | | | 623/23.72 |
| 2022/0220038 A1 | * | 7/2022 | Hashimoto | ............... A61F 2/28 |

FOREIGN PATENT DOCUMENTS

| | | | | | | |
|---|---|---|---|---|---|---|
| CN | 105084336 A | * | 11/2015 | | | |
| CN | 105084336 B | * | 9/2017 | | | |
| CN | 111803715 A | * | 10/2020 | | | |
| JP | 2020196649 A | * | 12/2020 | ............... | A61F 2/28 |
| WO | WO-2020008555 A1 | * | 1/2020 | | | |

OTHER PUBLICATIONS

Sánchez-Salcedo, S., Vila, M., Diaz, A. et al. Synthesis of HA/B-TCP bioceramic foams from natural products. J Sol-Gel Sci Technol 79, 160-166 (2016). https://doi.org/10.1007/s10971-016-4038-8 (Year: 2016).*

O.Gunduz, O. Kilic, N. Ekren, H. Gokce, C. Kalkandelen, F.N. Oktar. Natural Hydroxyapatite Synthesis from Fish Bones: "Atlantic Bonito" (Sarda sarda). Key Engineering Materials, Nov. 2016, vol. 720, pp. 207-209.

Sandra Sánchez-Salcedo, Mercedes Vila, Alfredo Diaz, Carlos Acosta, Ivan Barton, Andrea Escobar & Maria Vallet- Regi. Synthesis of HA/β-TCP bioceramic foams from natural products. Journal of Sol-Gel Science and Technology, vol. 79, pp. 160-166, (2016).

* cited by examiner

*Primary Examiner* — Sahana S Kaup
*Assistant Examiner* — Ashlee E Wertz
(74) *Attorney, Agent, or Firm* — Hannah Tien

(57) ABSTRACT

The present invention relates to a two-stage sintering method for preparing a porous biphasic calcium phosphate ceramic from calcium-containing biological waste, wherein hydroxyapatite prepared from calcium-containing waste is mixed with a foaming agent to prepare a bone graft material having medicinal use through two-stage sintering.

6 Claims, 8 Drawing Sheets

1

TWO-STAGE SINTERING METHOD FOR PREPARING POROUS BIPHASIC CALCIUM PHOSPHATE CERAMIC FROM CALCIUM-CONTAINING BIOLOGICAL WASTE

CROSS-REFERENCE TO RELATED APPLICATION

This application claims the benefit of Taiwanese Patent Application No. 110129795 filed Aug. 12, 2021, which is incorporated by reference herein in its entirety.

FIELD OF THE INVENTION

The present invention relates to a two-stage sintering method for preparing a porous biphasic calcium phosphate ceramic from calcium-containing biological waste, through pre-mixing hydroxyapatite material and a foaming agent, and using a foaming method and two-stage heating at different temperatures and two-stage heating for different time to obtain biphasic calcium phosphate with pores.

BACKGROUND OF THE INVENTION

The chemical formula of hydroxyapatite (HA) is $Ca_{10}(PO_4)_6(OH)_2$, the ideal calcium to phosphorus ratio is 1.67. It is provided with excellent biological activity, biocompatibility and osteoconductivity, and can form bonding with bone tissues. HA is non-toxic and does not cause inflammatory reactions in the body, so it is widely used for bone defect repairs and as substitute materials, plastic surgery filler materials, tissue engineering scaffolds and drug carriers, etc.

The technology of hydroxyapatite synthesis has been developed in many different ways, which can mainly be divided into liquid-phase synthesis methods and solid-phase synthesis methods. Solid-phase synthesis methods include solid-phase sintering method and ball milling method; and liquid-phase synthesis methods include sol-gel synthesis, micro-emulsion method, chemical precipitation method, hydrothermal method, microwave irradiation method, etc.

Compared to the hydroxyapatite synthesized by conventional chemical agents, natural oyster shells have a variety of trace elements, such as sodium, magnesium, strontium, etc. These trace elements are essential elements for human bone growth.

At present, the synthesis of hydroxyapatite in Taiwan is primarily dominated by using chemical agents. However, the biocompatibility of hydroxyapatite synthesized from natural wastes is better than those produced by using chemical agents, and can reduce rejections of human soft tissues such as skin, muscle and gum, allowing it to be an ideal component for bone graft and dental implant materials. Recently, it has been widely used in hard tissue repairs and applications including bone augmentation, bone repairs and surface coatings on metals.

According to the statistics on waste provided by the Council of Agriculture, Taiwan produced an average of about 190,000 metric tons of waste oyster shells annually from 2007 to 2017.

Waste oyster shells not only take up space, residual meats on the shells breed flies, which produces foul odors at high temperature under the sunlight, causing environmental pollution problems.

In the past, oyster shells were mainly used as feed, compost and cultivation media, the overall added value was not high.

SUMMARY OF THE INVENTION

In view of the above technical circumstances, the present invention provides a two-stage sintering method for preparing porous biphasic calcium phosphate ceramic from calcium-containing biological waste, comprising: a mixing and rotating step of mixing hydroxyapatite and a foaming agent into a mixture, and stirring the mixture at high speed into a foam shape; a drying step of drying the mixture the foam shape into a shaped mixture; a first-stage sintering step of heating the shaped mixture at 300 degrees to 900 degrees for 1 to 5 hours; and a second-stage sintering step of continually heating the shaped mixture after the first-stage sintering at 900 degrees to 1400 degrees for 0.1 to 30 hours to obtain a bone graft material containing the porous biphasic calcium phosphate ceramic.

The present invention also provides a porous biphasic calcium phosphate ceramic, comprising hydroxyapatite and beta-tricalcium phosphate, wherein the volume percentage of the hydroxyapatite is from 20% to 80%, and the volume percentage of the beta-tricalcium phosphate is from 20% to 80%.

The pore size of the porous biphasic calcium phosphate ceramic of the present invention is between 50 μm and 700 μm.

The present invention further provides a porous biphasic calcium phosphate ceramic to apply for bone graft, dental filling material.

DETAILED DESCRIPTION OF THE INVENTION

Figure 1:
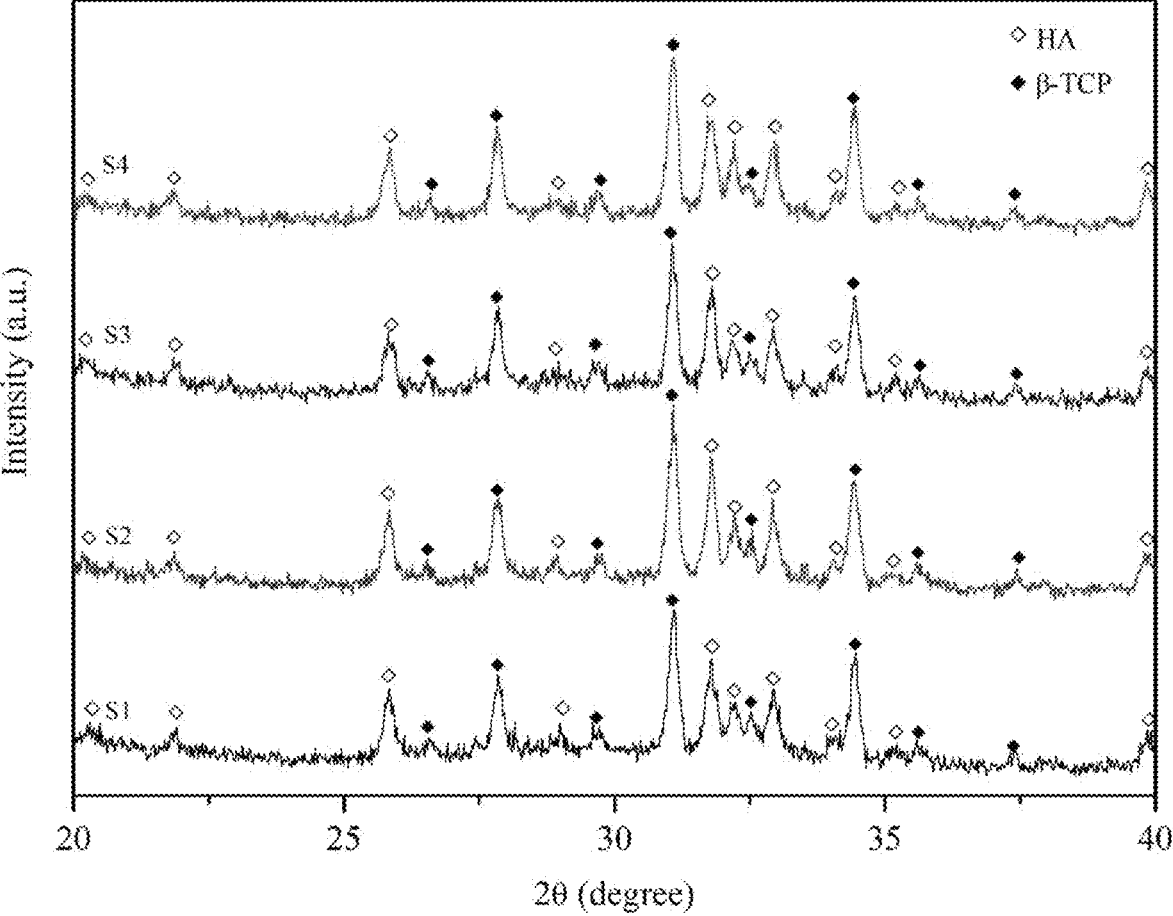
FIG. 1 is the X-ray diffractometer (XRD) diffraction patterns of porous biphasic calcium phosphate ceramics sintered at different holding temperatures and time.

As used herein, "a," "an," "the," "at least one," and "one or more" are used Interchangeably.

The present invention uses waste oyster shells as raw materials to prepare hydroxyapatite. The preparation process changes the waste oyster shells into a bone graft material having biphasic hydroxyapatite/beta-tricalcium phosphate through changes in its phase. It can further enhance the added value of waste oyster shells, and mitigate the environmental pollution problems caused by them.

According to the purpose of the present invention, the composition of the hydroxyapatite crystal structure synthesized by using the biological calcium-containing raw material such as oyster shells, is much closer to human bone, as a result, the biocompatibility is higher.

According to the embodiment of the present invention, the following steps are included: a mixing and rotating step, a drying step, a first-stage sintering step and a second-stage sintering step.

In the mixing and rotating step, hydroxyapatite and a foaming agent are mixed into a mixture at a ratio from 10% to 90% to 90% to 10%, and the mixture is mixed at a high speed of 250 to 3000 rpm to form a foam shape, wherein a preferred mixing ratio is from 15% to 85% to 85% to 15%.

In the drying step, the foam-shaped mixture after the mixing and rotating step is dried at 50-200 degrees to form a shaped mixture.

In the first-stage sintering step, the shaped mixture is heated at a holding temperature of 300 degrees to 900 degrees for 1 to 5 hours, wherein a holding temperature condition for a better sintering effect is heating at a temperature of 500 degrees to 800 degrees for 2 to 4 hours.

The second-stage sintering step, the shaped mixture after the first-stage sintering continues to be heated at a holding temperature of 900 degrees to 1400 degrees for 0.1 to 30 hours to obtain a bone graft material containing porous biphasic calcium phosphate ceramic, wherein the holding temperature condition for a better sintering effect is heating at a temperature of 1000 degrees to 1200 degrees for 15 to 30 hours.

According to the embodiment of the present invention, the prepared biphasic calcium phosphate has physical characteristics including a porosity of 40-95% and a pore size of 50-700 μm.

According to the embodiment of the present invention, the prepared biphasic calcium phosphate contains hydroxyapatite and beta-tricalcium phosphate components, the content of the hydroxyapatite (volume percentage) is from 20% to 80%, and the content of beta-tricalcium phosphate (volume percent) is from 20% to 80%.

According to the embodiment of the present invention, the pores larger than 100 μm and smaller than 100 μm can be produced so as to satisfy the applicability of porous implants, and the pores larger than 100 μm can cause ingrowth of bone tissues. In addition, the hydroxyapatite powder, after being sintered, forms necking to be connected with each other, indicating that the powders are bonded to each other so that they can provide the strength required for surgical procedures.

According to the embodiment of the present invention, the hydroxyapatite crystal grain size is between 32 nm and 146 nm.

According to the embodiment of the present invention, the beta-tricalcium phosphate crystal grain size is between 37 nm and 49 nm.

According to the embodiment of the present invention, the crystallinity of the hydroxyapatite is higher than 62%.

The waste material of the present invention includes but is not limited to egg shells, crustacean crab shells, shrimp shells, lobster shells, freshwater lobster shells and krill shells, bivalvia oyster shells, oyster shells, clam shells, gastropoda abalone shells.

Another aspect of the present invention provides a biomedical material and a preparation method, including but not limited to bone materials and dental materials.

Another aspect of the present invention provides a calcium-phosphorus compound containing sodium, magnesium and strontium and a preparation method thereof.

EXAMPLE

The following examples are non-limited and are merely representative of various aspects and features of the present invention.

Example 1: XRD Diffraction

After grinding the samples into powder, phase analysis was performed by an X-ray diffraction analyzer (XRD; D8, Bruker, Germany) with Cu K-alpha radiation of wavelength 0.15406 nm. The operating voltage is 30 kV, and the operating current is 30 mA. The scanning speed is set to 2°/min, and the diffraction angle is 20°-40°.

According to a preferred embodiment of the present invention, 1 gram of hydroxyapatite was mixed with 1.5 ml of a foaming agent, wherein the foaming agent included but was not limited to coconut oil foaming agent, glucose foaming agent (decyl glucosamine), amino acid foaming agent (TEA cocoyl glutamate), weak acid foaming agent (ammonium lauryl sulfate), sodium lauroyl sarcosinate, fatty alcohol surfactant (fatty alcohol ethoxylate).

As shown in FIG. 1, the XRD diffraction patterns of the porous biphasic calcium phosphate ceramic of the present invention sintered at different holding temperatures and time were shown. Through the diffraction patterns, the phase ratios between hydroxyapatite and beta-tricalcium phosphate, two-stage sintering temperatures and time were obtained and shown in Table 1 below.

Table 1 Phase ratios, crystal grain sizes and crystallinity of the porous biphasic calcium phosphate ceramic after being sintered at different holding temperatures and time.

| | S1 | S2 | S3 | S4 |
|---|---|---|---|---|
| first-stage sintering temperature/time | 700 degrees/ 2 hours | 700 degrees/ 2 hours | 700 degrees/ 2 hours | 700 degrees/ 2 hours |
| second-stage sintering temperature/time | 900 degrees/ 1 hour | 900 degrees/ 4 hours | 900 degrees/ 5 hours | 900 degrees/ 6 hours |
| ratio of hydroxyapatite:beta-tricalcium phosphate | 42:58 | 45:55 | 44:46 | 45:55 |
| hydroxyapatite crystal grain size (nm) | 36 | 49 | 34 | 35 |
| beta-tricalcium phosphate crystal grain size (nm) | 49 | 43 | 49 | 49 |
| hydroxyapatite crystallinity (%) | 71 | 69 | 75 | 73 |

According to a preferred embodiment of the present invention, 1 gram of hydroxyapatite was mixed with 1.5 ml of a foaming agent, wherein the foaming agent was the coconut oil.

Figure 2:
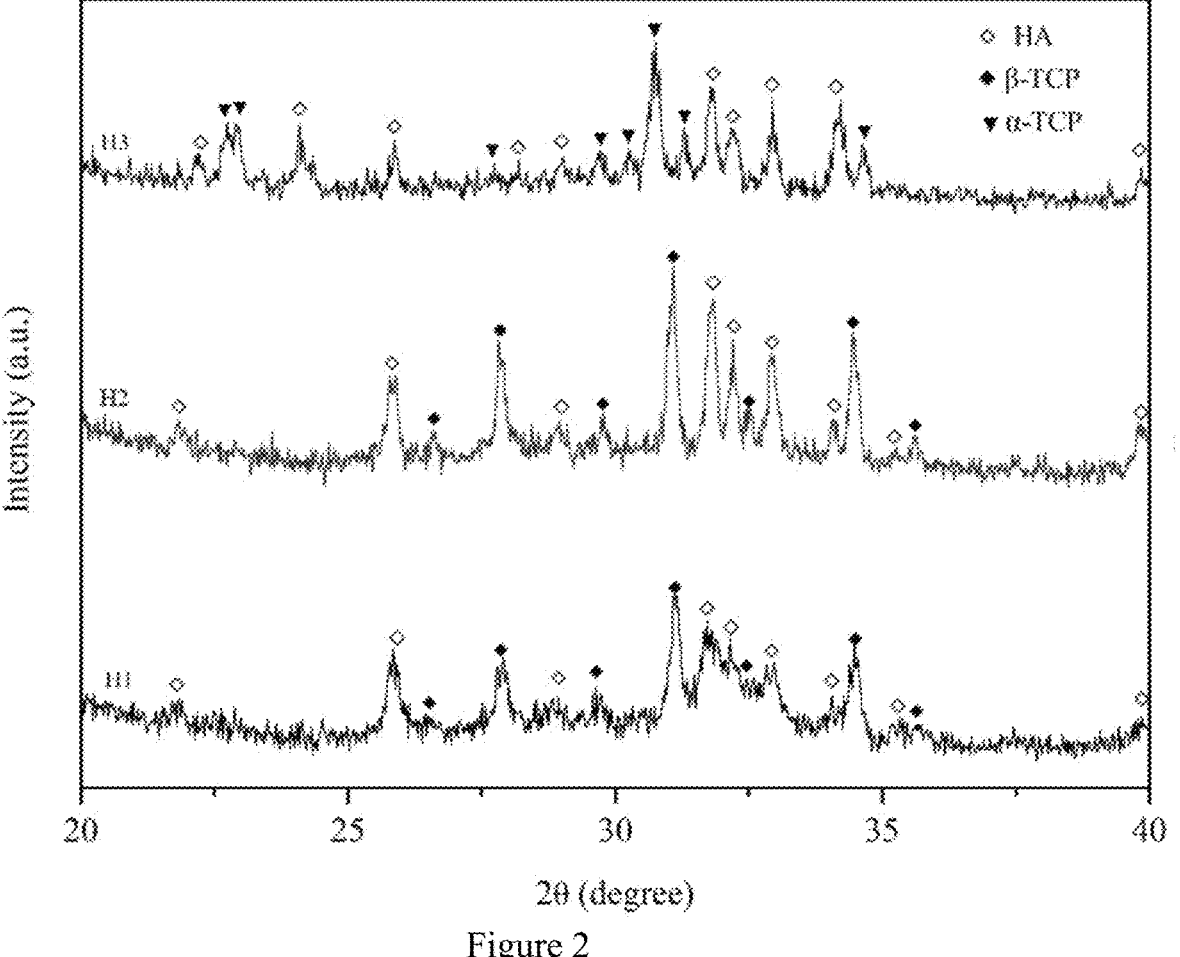
FIG. 2 is the XRD diffraction patterns of porous biphasic calcium phosphate ceramics sintered at different holding temperatures and time.

As shown in FIG. 2, the XRD diffraction patterns of the porous biphasic calcium phosphate ceramic of the present invention sintered at different holding temperatures and time were shown. Through the diffraction patterns, the phase ratios between hydroxyapatite and beta-tricalcium phosphate, two-stage sintering temperatures and time were obtained and shown in Table 2 below.

Table 2 Phase ratios, crystal grain sizes and crystallinity of the biphasic porous calcium phosphate ceramic after being sintered at different holding temperatures.

| | H1 | H2 | H3 |
|---|---|---|---|
| first-stage sintering temperature/time | 700 degrees/ 2 hours | 700 degrees/ 2 hours | 700 degrees/ 2 hours |
| second-stage sintering temperature/time | 700 degrees/ 4 hours | 1200 degrees/ 4 hours | 1400 degrees/ 4 hours |
| ratio of hydroxyapatite:beta-tricalcium phosphate | 51:49 | 47:53 | HA + alpha-TCP |
| hydroxyapatite crystal grain size (nm) | 32 | 36 | 146 |
| beta-tricalcium phosphate crystal grain size (nm) | 37 | 37 | 49 |
| hydroxyapatite crystallinity (%) | 62 | 92 | 95 |

According to a preferred embodiment of the present invention, 1 gram of hydroxyapatite was mixed with 1.5 ml of a foaming agent, wherein the foaming agent was the coconut oil.

Figure 3:
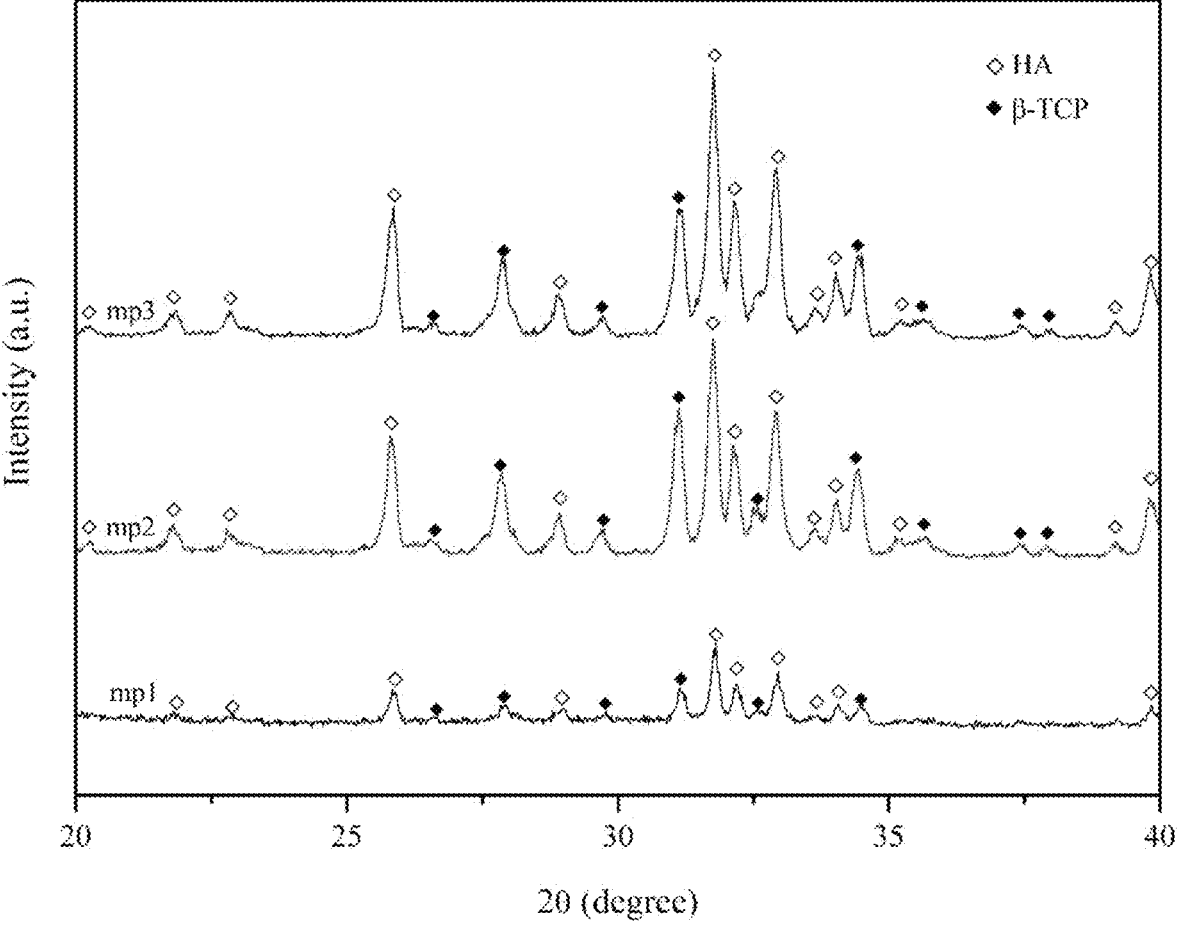
FIG. 3 is the XRD diffraction patterns of the porous biphasic calcium phosphate ceramics sintered at different holding temperatures and time.

As shown in FIG. 3, the XRD diffraction patterns of the porous biphasic calcium phosphate ceramic of the present invention sintered at different holding temperatures and time were shown. Through the diffraction pattern, biphasic ratios between hydroxyapatite and beta-tricalcium phosphate, two-stage sintering temperatures and time were obtained and shown in Table 3 below.

Table 3 Phase ratios, crystal grain sizes and crystallinity of the porous biphasic calcium phosphate ceramic after being sintered at different holding time.

| | mp1 | mp2 | mp3 |
|---|---|---|---|
| first-stage sintering temperature/time | 700 degrees/ 2 hours | 700 degrees/ 2 hours | 700 degrees/ 2 hours |
| second-stage sintering temperature/time | 1000 degrees/ 20 hours | 1000 degrees/ 25 hours | 1000 degrees/ 30 hours |
| ratio of hydroxyapatite:beta-tricalcium phosphate | 67:33 | 62:38 | 55:45 |
| hydroxyapatite crystal grain size (nm) | 49 | 50 | 38 |
| beta-tricalcium phosphate crystal grain size (nm) | 49 | 38 | 38 |
| hydroxyapatite crystallinity (%) | 89 | 90 | 92 |

According to one embodiment of the present invention, the content of hydroxyapatite (volume percentage) was from 20% to 80%, and the content of beta-tricalcium phosphate (volume percentage) was from 20% to 80%, wherein the preferred ones were 62% and 38%, respectively.

According to one embodiment of the present invention, the crystal grain sizes of the hydroxyapatite were all between 32 nm and 146 nm, preferably 38, 49, and 50 nm.

According to one embodiment of the present invention, the crystal grain sizes of beta-tricalcium phosphate were all between 37 nm and 49 nm, and preferably 37, 38, and 49 nm.

According to one embodiment of the present invention, the first-stage sintering temperature and time were 700 degrees and 2 hours, wherein the preferred second-stage sintering temperature was 1000 degrees, and the preferred sintering time was 25 hours. Subsequent analyses were conducted under this condition.

Example 2: FTIR Analysis

The chemical compositions of the samples were analyzed using a Fourier transform infrared spectrometer (FTIR; Cary 630, Agilent, Santa Clara, USA) through a typical KBr pellet technique, and the infrared spectra were obtained with a wavenumber range of 600-4000 cm$^{-1}$.

Figure 4:
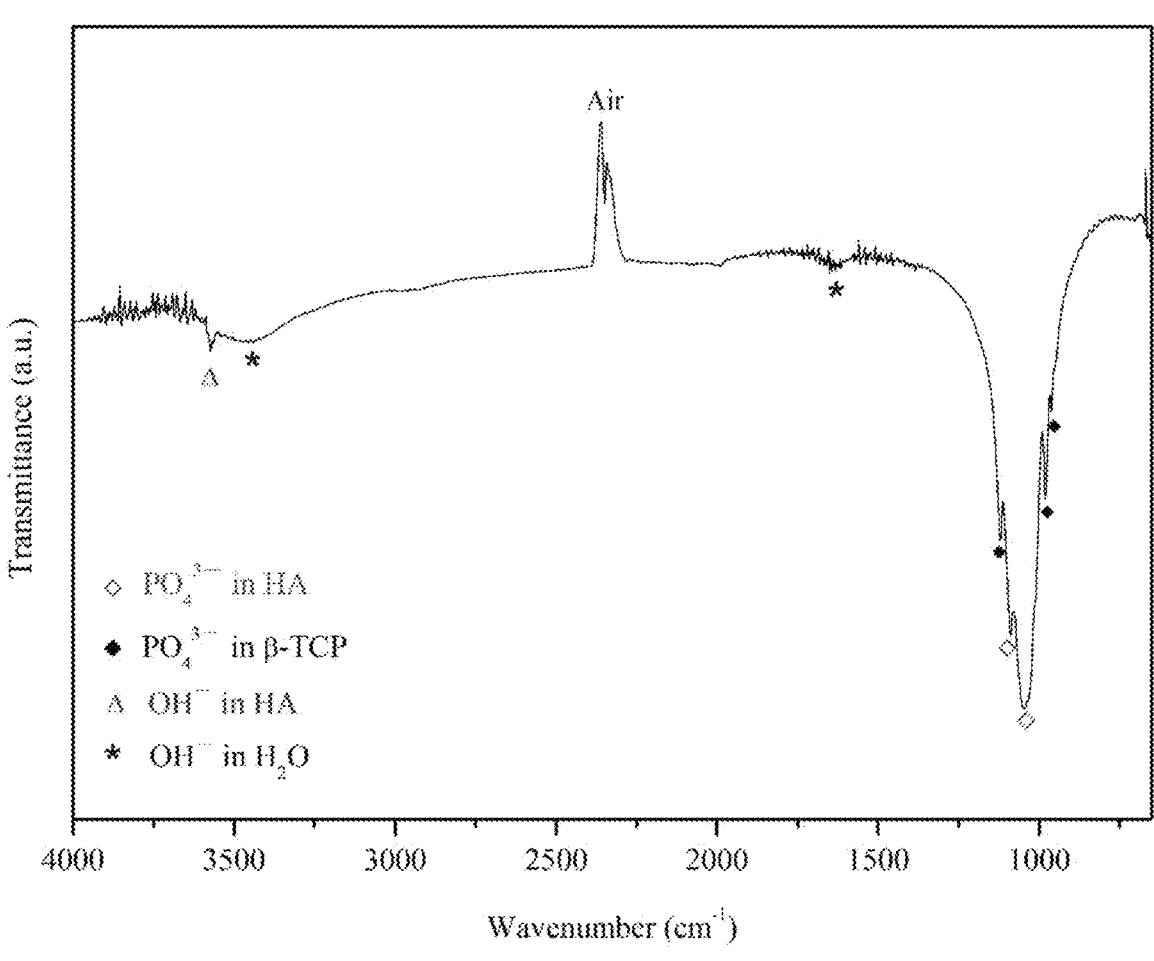
FIG. 4 is the Fourier-transform infrared spectroscopy (FTIR) analysis of the porous biphasic calcium phosphate ceramic.

As shown in FIG. 4, graph of the FTIR analysis results of the porous biphasic calcium phosphate ceramic of the present invention was shown. Through comparison of the functional groups, the sintered products having biphasic calcium phosphate according to the present invention, including OH group and $PO_4^{3-}$ groups.

Example 3: FESEM Imaging

The surface of the sample was coated with platinum (current was 10 mA, sputtering time was 50 seconds), and the microscopic morphology of the sample under different magnifications was observed by scanning electron microscope (FE-SEM; S-4800, Hitachi, Japan).

Figure 5:
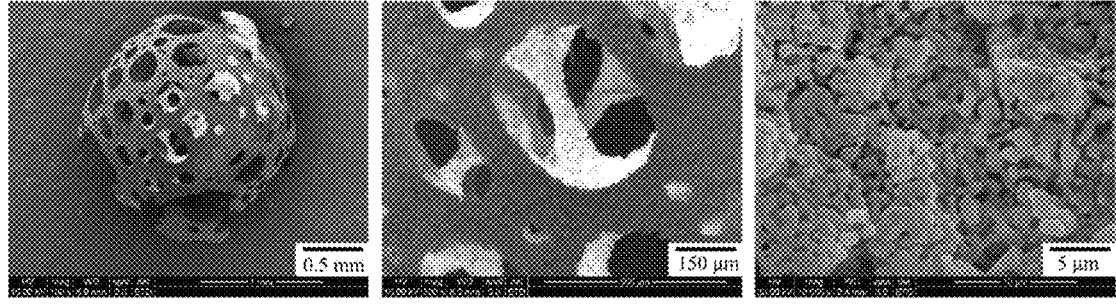
FIG. 5 is the field emission scanning electron microscope (FESEM) images of the porous biphasic calcium phosphate ceramic.

As shown in FIG. 5, FESEM images of the porous biphasic calcium phosphate ceramic was shown of the present invention. It was found that the crystalline particles after the sintering of the present invention had porosity, and many pores were larger than 100 μm. In addition, it could be found from the images that the pores had connectivity, the pore on the side could be observed through the pore on the other site.

Figure 6:
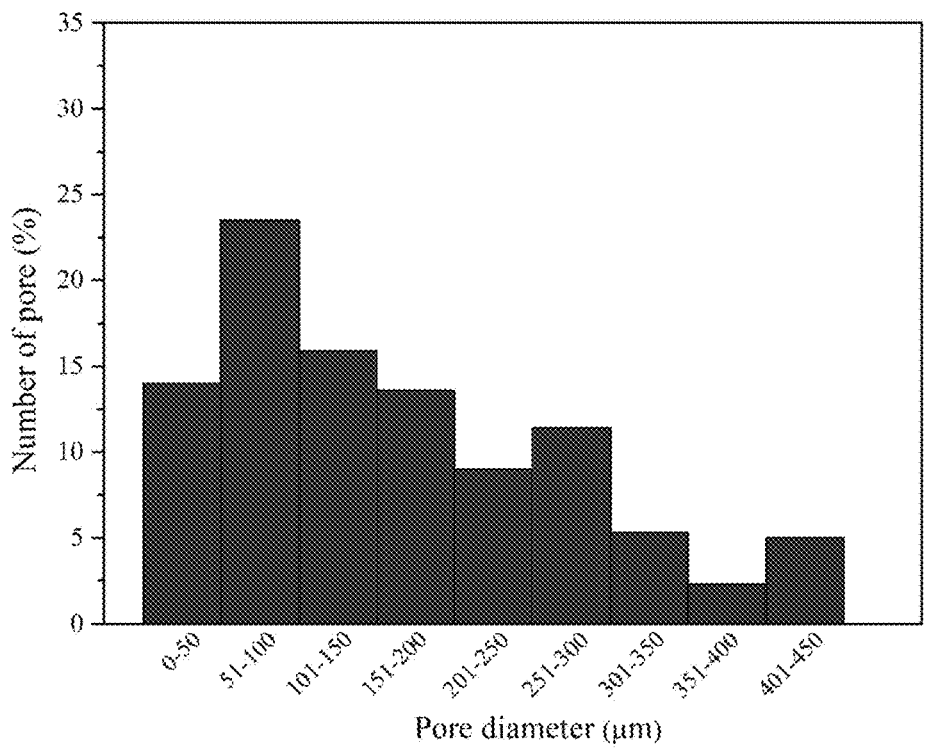
FIG. 6 is the pore diameter distribution of the porous biphasic calcium phosphate ceramic.

As shown in FIG. 6, the pore diameter distribution of the porous biphasic calcium phosphate ceramic was shown. Through an image analysis method, the average diameter was used to represent the pore diameter distribution of the porous ceramic particles prepared by the present invention, and more than 60% of the pores of the porous ceramic particles prepared by the present invention had an average pore diameter greater than 100 μm.

Figure 7:
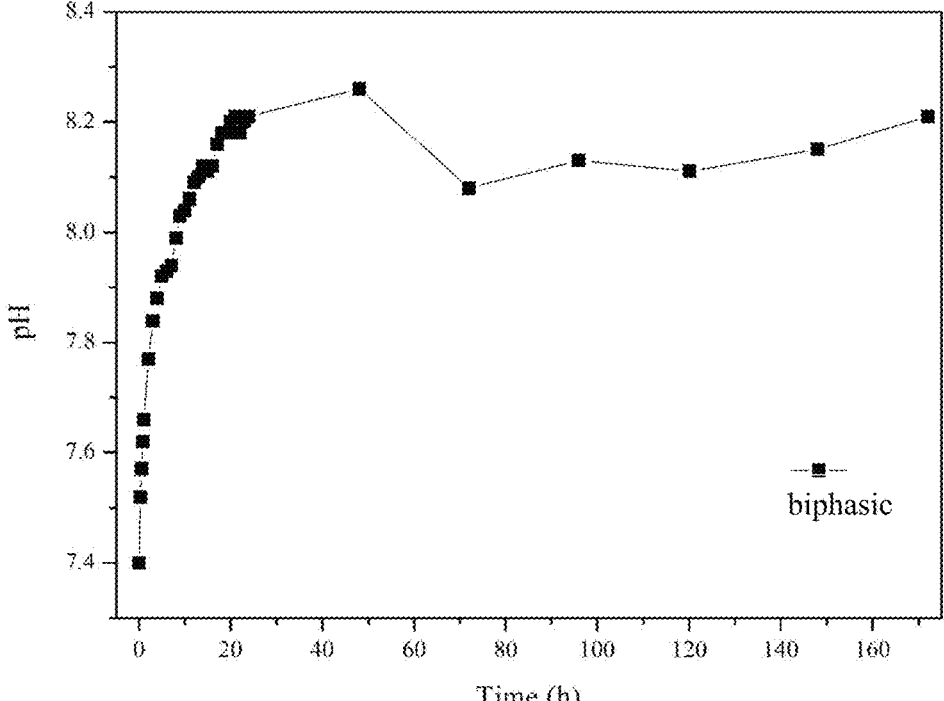
FIG. 7 is the pH changes of the porous biphasic calcium phosphate ceramic immersed in simulated body fluid (SBF).

As shown in FIG. 7, it shows a graph of the pH changes of the porous biphasic calcium phosphate ceramic immersed in simulated body fluid, simulating the human body environment. The pH changes of the porous ceramic particles prepared by the present invention tended to be stabilized after 80 hours, indicating that the degradation and deposition reached equilibrium.

The ion concentrations of the simulated body fluid (SBF) were nearly equal to those of blood plasma. The SBF was prepared by dissolving reagent grade NaCl (8.035 g/L), NaHCO$_3$ (0.355 g/L), KCl (0.225 g/L), K$_2$HPO$_4$·3H$_2$O (0.231 g/L), MgCl$_2$·6H$_2$O (0.311 g/L), CaCl$_2$ (0.292 g/L), and Na$_2$SO$_4$ (0.072 g/L) in distilled water. The solution was buffered at pH 7.4 with tris(hydroxylmethyl)aminomethane ((CH$_2$OH)$_3$CNH$_2$) and 1 M hydrochloric acid (HCl) at 36·5±1 degrees.

Figure 8:
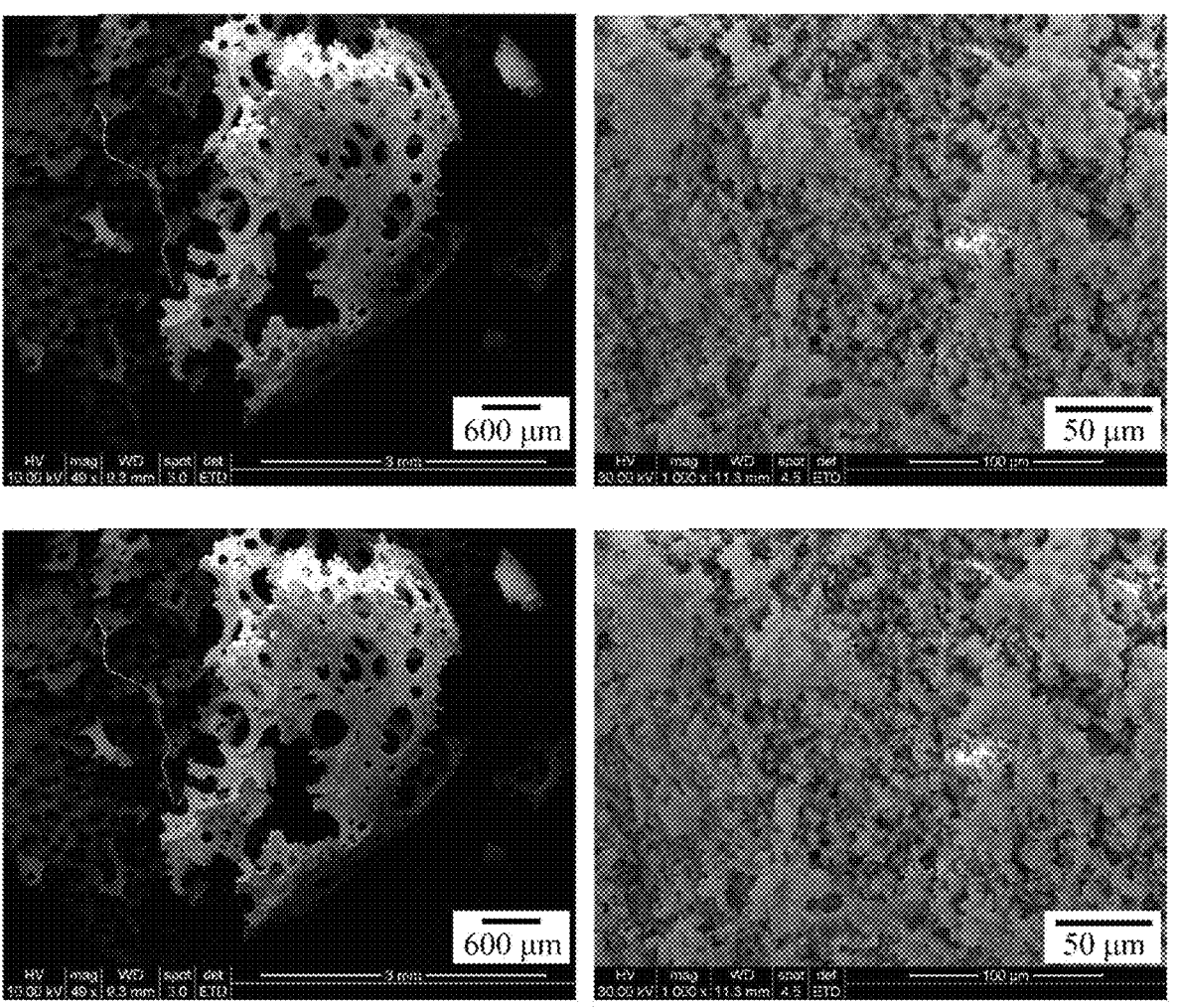
FIG. 8 is FESEM images of the porous biphasic calcium phosphate ceramics immersed in SBF for 7 days.

As shown in FIG. 8, FESEM images of the porous biphasic calcium phosphate ceramic after being immersed in SBF for 7 days were shown. After the porous ceramic particles prepared by the present invention were immersed in simulated body fluid for 7 days, apatite was deposited on the surface, which could be used for bone tissues to form bonding, and the material prepared by the present invention had biological activity.

Example 4: MTT Assay

The cytotoxicity assay was performed according to the regulation of ISO10993-5. The sample were extracted for cytotoxic evaluation. The samples (H, H/B, commercial bone graft) were soaked in the medium for 24 hours at the ratio of 0.2 g/mL The samples were further diluted at different ratios (100, 50, 25, 12.5%) and cultured with L929 fibroblasts at 37 degrees for 1 day.

Figure 9:
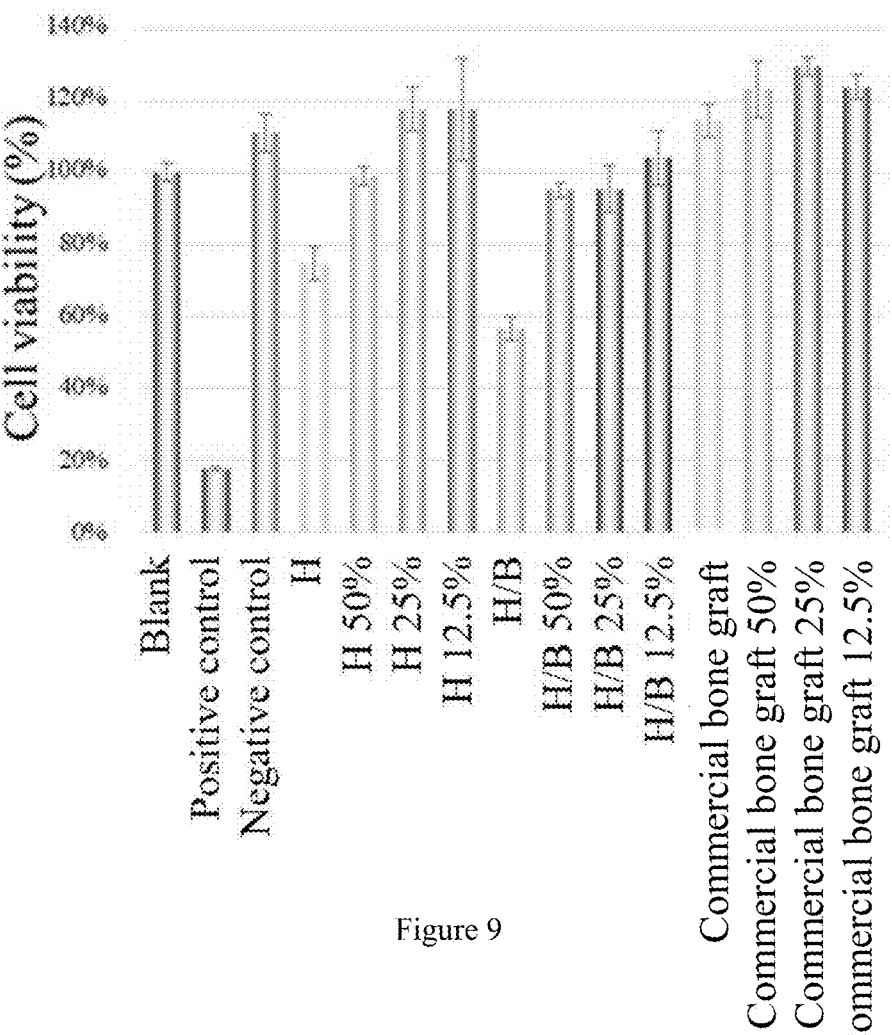
FIG. 9 is the MTT cell viability assay.

As shown in FIG. 9, the graph of the cell viability assay (3-(4,5-Dimethylthiazol-2-yl)-2,5-diphenyltetrazolium bromide, MTT) was shown for evaluating cytotoxicity.

The samples in this experiment were H, H/B, and commercial bone graft, wherein the H sample was water-dissolved oyster shells, the hydroxyapatite was synthesized through the precipitation method for a reaction of 30 min, and after being foamed and sintered at 1300 degrees for 20 minutes, the single-phase porous HA particles were obtained; the H/B sample was acetic-dissolved oyster shells, hydroxyapatite was synthesized through the precipitation method for a reaction of 12 hours, and after being foamed and sintered at 1000 degrees for 25 hours, the porous biphasic apatite particles were obtained; the positive control group was phenol; and the negative control group was aluminum oxide.

The samples (H, H/B, commercial bone graft) at a ratio of 0.2 g/mL were immersed in a medium for 24 hours of extraction, and diluted the ratio to 100, 50, 25, 12.5%, and were co-cultured with L929 fibroblasts at 37 degrees for 1 day.

The results of the cytotoxicity test of the porous biphasic calcium phosphate ceramic prepared by the present invention showed that, except for the undiluted samples, no cytotoxicity was found in the remaining dilutions at ratios of 50, 25, and 12.5%.

Example 5: Mouse Precursor Stein Cell Culturing

Osteocyte activity assessment was performed by using D1 mouse precursor stein cells. The samples were extracted at 25% for 24 hours in culture medium, and then D1 mouse precursor stein cells were cultured for 1, 7, and 14 days in the medium.

Example 6: WST Assay

After culturing the D1 mouse precursor stein cell for 1, 7, and 14 days, the absorbance at 450 nm was measured with WST reagent co-culturing for 2 hours. The higher the absorbance, the higher the number of cells are active.

Figure 10:
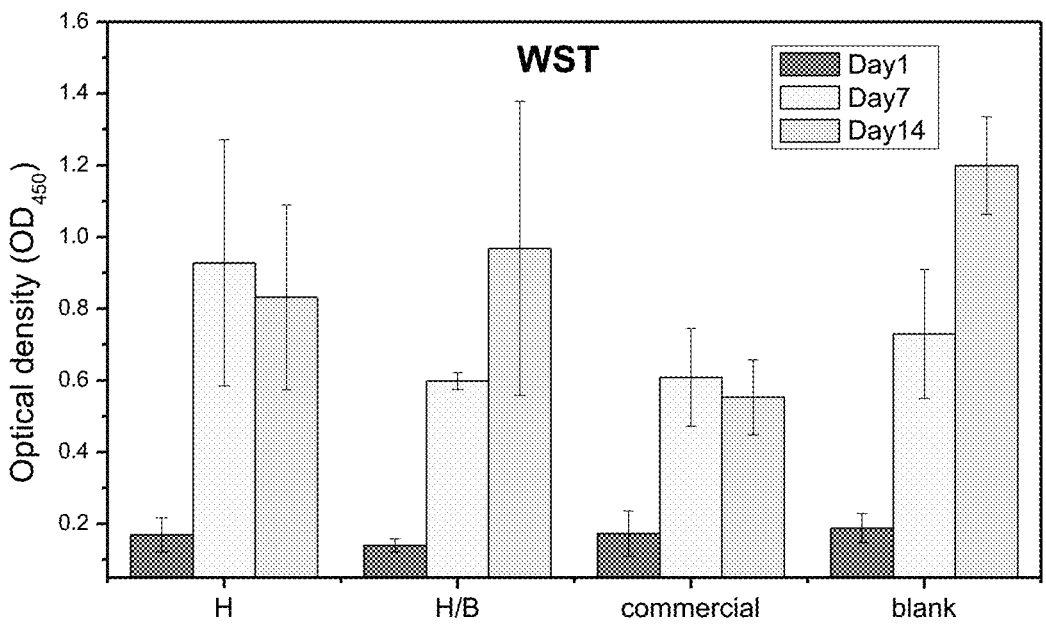
FIG. 10 is the WST-8 cell activity test of D1 mouse precursor stein cells on day 1, day 7 and day 14.

As shown in FIG. 10, the WST-8 cell viability assay of the mouse precursor stein cells on day 1, day 7, and day 14 were shown, respectively.

The materials of the experimental group were extracted with 25% medium for 24 hours, the concentration was equivalent to 50 mg/mL, co-cultured with D1 cells for 1, 7, and 14 days, incubated with the WST reagent for 2 hours and then the absorbance was measured at 450 nm.

For the cell viability of the mouse precursor stein cells, the porous biphasic calcium phosphate ceramic prepared by the present invention was better than the commercial kit on day 14.

Example 7: ALP Phosphatase Assay

The differentiation ability of the osteoblasts was determined by the activity of the alkaline phosphatase. D1 mouse stein cells cultured for 1, 7, and 14 days were used to evaluate the primary bone differentiation ability of the sample extract.

Figure 11:
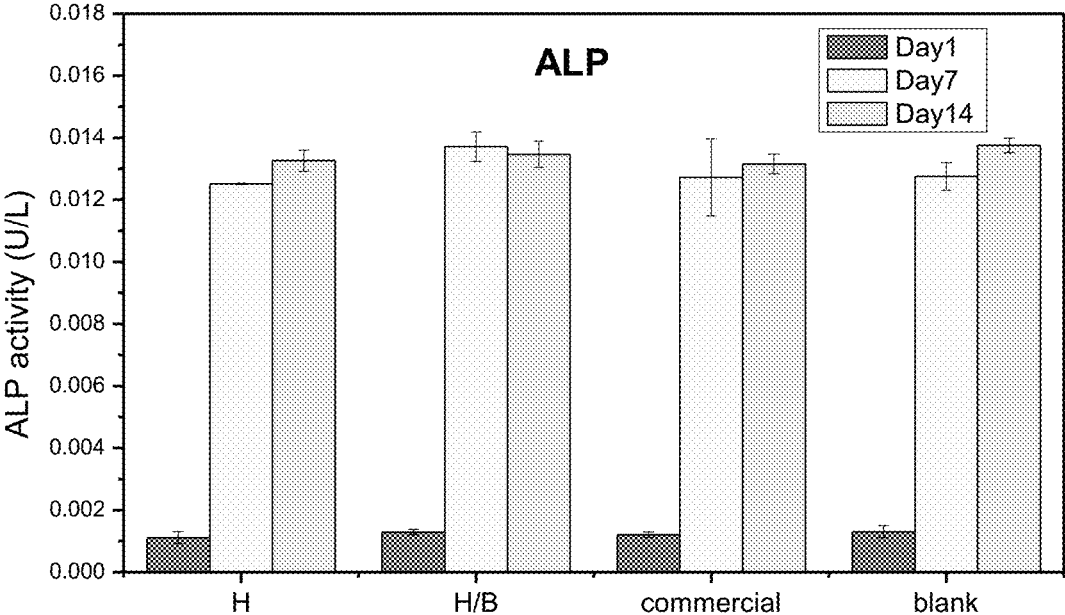
FIG. 11 is the ALP bone differentiation test of D1 mouse precursor stein cells on day 1, day 7 and day 14.

As shown in FIG. 11, the bone differentiation test of the activity of alkaline phosphatase under fluorescence (Alkaline Phosphatase Assay Kit, ALP) of the D1 mouse precursor stein cells on day 1, day 7, and day 14 were shown, respectively.

For the bone differentiation activity of the mouse precursor stein cells, the porous biphasic calcium phosphate ceramic prepared by the present invention was better than the commercial kit on day 7.

While the invention has been described and exemplified in sufficient details for those skilled in this art to make and use it, various alternatives, modifications, and improvements should be apparent without departing from the spirit and scope of this invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A two-stage sintering method for preparing a porous biphasic calcium phosphate ceramic from calcium-containing biological waste, comprising:
 a mixing and rotating step of mixing hydroxyapatite and a foaming agent into a mixture, and stirring the mixture at high speed into a foam shape;
 a drying step of drying the mixture of the foam shape into a shaped mixture;
 a first-stage sintering step of heating the shaped mixture at 300° C. to 900° C. for 1 to 5 hours; and
 a second-stage sintering step of continually heating the shaped mixture after the first-stage sintering at 1000° C. to 1200° C. for 15 to 30 hours to obtain a bone graft material containing the porous biphasic calcium phosphate ceramic.

2. The two-stage sintering method for preparing porous biphasic calcium phosphate ceramic from calcium-containing biological waste of claim 1, wherein the calcium-containing biological waste is egg shells, crustacean crab shells, shrimp shells, lobster shells, freshwater lobster shells and krill shells, bivalvia oyster shells, oyster shells, clam shells, or gastropoda abalone shells.

3. The two-stage sintering method for preparing porous biphasic calcium phosphate ceramic from calcium-containing biological waste of claim 1, wherein the foaming agent of the mixing and rotating step is coconut oil foaming agent, glucose foaming agent, amino acid foaming agent, weak acid foaming agent, sodium lauroyl sarcosinate, fatty alcohol surfactant or a combination thereof.

4. The two-stage sintering method for preparing porous biphasic calcium phosphate ceramic from calcium-containing biological waste of claim 1, wherein the mixing ratio of the hydroxyapatite and the foaming agent of the mixing and rotating step is from 10% to 90% to 90% to 10%.

5. The two-stage sintering method for preparing porous biphasic calcium phosphate ceramic from calcium-containing biological waste of claim 1, wherein the high speed of the mixing and rotating step is from 250 to 3000 rpm.

6. The two-stage sintering method for preparing porous biphasic calcium phosphate ceramic from calcium-containing biological waste of claim 1, wherein the drying temperature of the drying step is from 50 to 200° C.

\* \* \* \* \*